United States Patent
Morikawa et al.

(10) Patent No.: US 8,546,770 B2
(45) Date of Patent: Oct. 1, 2013

(54) CHARGED PARTICLE BEAM DEVICE AND SAMPLE OBSERVATION METHOD

(75) Inventors: Akinari Morikawa, Hitachinaka (JP); Takeshi Sato, Hitachinaka (JP); Eiko Nakazawa, Mito (JP); Susumu Kuwabata, Ibaraki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/515,717

(22) PCT Filed: Nov. 11, 2010

(86) PCT No.: PCT/JP2010/006640
§ 371 (c)(1),
(2), (4) Date: Aug. 7, 2012

(87) PCT Pub. No.: WO2011/074178
PCT Pub. Date: Jun. 23, 2011

(65) Prior Publication Data
US 2012/0292507 A1 Nov. 22, 2012

(30) Foreign Application Priority Data
Dec. 14, 2009 (JP) .................................. 2009-282431

(51) Int. Cl.
*H01J 40/00* (2006.01)
*H01J 47/00* (2006.01)

(52) U.S. Cl.
USPC ...... 250/440.11; 250/306; 250/307; 250/310; 250/311; 250/396 R; 359/391

(58) Field of Classification Search
USPC ........ 250/305–307, 310, 311, 396 R, 440.11; 359/391
See application file for complete search history.

(56) References Cited

U.S. PATENT DOCUMENTS

| | | | |
|---|---|---|---|
| 2007/0145268 A1* | 6/2007 | Chao et al. | .................. 250/310 |
| 2009/0173882 A1 | 7/2009 | Kuwabata et al. | |
| 2011/0057100 A1 | 3/2011 | Nakazawa et al. | |

FOREIGN PATENT DOCUMENTS

| | | |
|---|---|---|
| EP | 1 978 355 A1 | 10/2008 |
| JP | 2009-68071 A | 4/2009 |

(Continued)

OTHER PUBLICATIONS

Corresponding International Search Report with English Translation dated Jan. 25, 2011 ( ten (10) pages).

(Continued)

*Primary Examiner* — Jack Berman
*Assistant Examiner* — Meenakshi Sahu
(74) *Attorney, Agent, or Firm* — Crowell & Moring LLP (57) ABSTRACT

There is provided a charged particle beam device which has a mechanism adjusting the shape of an ionic liquid droplet to be adhered to a sample and the thickness of a film of the ionic liquid, in such a manner that they are suitable for various types of observations by an electronic microscope and the like, and for processing using ion beams. The charged particle beam device is characterized in that it includes an ionic liquid holding member having an opening, an ionic liquid supplying unit for filling an ionic liquid into the opening, an observation unit for observing an adhesion state of the ionic liquid, and charged particle beam generating units for radiating charged particle beams, and can adjust the thickness of an ionic liquid droplet to be filled in the opening, when the charged particle beam device observes a sample in a state where it is floating in the ionic liquid by being dispersed into the ionic liquid or on a surface of the ionic liquid.

20 Claims, 8 Drawing Sheets

(56) References Cited

FOREIGN PATENT DOCUMENTS

| | | |
|---|---|---|
| JP | 2009-87594 A | 4/2009 |
| JP | 2009-128045 A | 6/2009 |
| JP | 2009-266741 A | 11/2009 |
| WO | WO 2007/083756 A1 | 7/2007 |
| WO | WO 2009/133842 A1 | 11/2009 |

OTHER PUBLICATIONS

Japanese Notice of Rejection with partial English translation dated Dec. 25, 2012 (ten (10) pages).

* cited by examiner

CHARGED PARTICLE BEAM DEVICE AND SAMPLE OBSERVATION METHOD

TECHNICAL FIELD

The present invention relates to a charged particle beam device and a sample observation method using the same.

BACKGROUND ART

An Ionic liquid is a salt in a liquid state at normal temperature and is characterized in that its vapor pressure is as close to zero as possible and its liquid state is kept even if it is heated and is in vacuum. To use this characteristic for operation and observation in a vacuum chamber has been considered.

Patent Literature 1 discloses a charge-up prevention liquid medium for an electronic microscope, which is composed of a cation and an anion, and an ionic liquid as an essential component and is impregnated in an entire sample for a scanning type electronic microscope (SEM) or an entire sample for a transmission type electronic microscope (TEM), or is applied onto an electron irradiation surface thereof, and imparts electroconductivity to the electron irradiation surface.

Moreover, Patent Literature 2 discloses a device which is provided with an ionic liquid storage tank, an electron spray device having a needle-shaped conductive capillary, and an ionic liquid recovery device, and emits a solution containing an ionic liquid into a gas phase using an electro spray method and generates an ion beam.

CITATION LIST

Patent Literature

Patent Literature 1: International Publication No. WO2007/083756
Patent Literature 2: Japanese Patent Laid-Open No. 2009-87594

SUMMARY OF INVENTION

Technical Problem

It is an object of the present invention to provide a charged particle beam device which has a mechanism for adjusting the shape of an ionic liquid droplet to be adhered to a sample and the thickness of a film of the ionic liquid such that they are suitable for various types of observations using an electronic microscope or the like and for processing using ion beams.

Solution to Problem

A charged particle beam device according to the present invention includes an ionic liquid holding member having an opening; an ionic liquid supplying unit for filling an ionic liquid into the opening; an observation unit for observing an adhesion state of the ionic liquid; and a charged particle beam generating unit for radiating charged particle beams, and can adjust the thickness of an ionic liquid droplet to be filled in the opening.

Advantageous Effects of Invention

According to the present invention, it is possible to easily adjust the shape of the ionic liquid droplet to be adhered to the sample, and the thickness of a film of the ionic liquid.

Moreover, according to the present invention, it is possible to form an ionic liquid in a superthin film-state which is suitable for high-resolution observation at an atomic level.

DESCRIPTION OF EMBODIMENTS

An embodiment according to the present invention is directed to a charged particle beam device which has a mechanism for adjusting the shape of an ionic liquid droplet to be adhered to a sample and the thickness of a film of the ionic liquid such that they are suitable for various types of observations by an electronic microscope. Particularly, the embodiment is directed to a charged particle beam device which forms an ionic liquid in a superthin film-state which is suitable for high-resolution observation at an atomic level using TEM.

In this embodiment, there are employed a device which can perform micromachining at a micrometer level for making an opening in an ionic liquid holding member, such as an FIB device; one or more mechanical probes (merely referred to as "probes") which perform operations at the micrometer level for filling an ionic liquid into the opening or applying the ionic liquid to the opening; and an observation device (referred to as "observation unit") which can observe the operations, such as SEM.

The charged particle beam device is adapted to observe a sample in a state, where the sample is floating in the ionic liquid by being dispersed in the ionic liquid or on a surface of the ionic liquid and, to this end, is adapted to be capable of adjusting the thickness of the ionic liquid droplet to be filled in the opening.

In the charged particle beam device, an ionic liquid supplying unit is configured as a mechanical probe which includes an ionic liquid portioning part for portioning a fraction of the ionic liquid from a pallet storing the ionic liquid and for filling the fraction of the ionic liquid into the opening, an arm part for moving the ionic liquid portioning part, and a support part for supporting the arm part. Moreover, the ionic liquid portioning part is configured so as to be capable of mainly filling the ionic liquid in the opening.

In the charged particle beam device, the shape of the ionic liquid portioning part is a flat plate-shape, a curved surface-shape, or a needle-shape.

The charged particle beam device employs an ink j et nozzle as the ionic liquid supplying unit.

The charged particle beam device has a sample supplying unit for dispersing a sample in the ionic liquid or on a surface of the ionic liquid.

In the charged particle beam device, the inner diameter of the opening is 1 to 10 μm.

In the charged particle beam device, the thermal conductivity of the ionic liquid is higher than the thermal conductivity of the sample.

In the charged particle beam device, the ionic liquid holding member, the ionic liquid supplying unit, the observation unit, and charged particle beam generating units are installed inside a chamber which can keep them in a pressure reduced-state.

The embodiment is also directed to a sample observation method which includes anionic liquid adhering step of adhering an ionic liquid to a solid sample, and a surface observing step of magnifying and observing a surface of the solid sample, wherein the ionic liquid adhering step includes a step of forming an ionic liquid in the form of a thin film on at least a part of the surface of the solid sample.

In the sample observation method, the ionic liquid adhering step includes an ionic liquid portioning step of portioning a fraction of the ionic liquid from a pallet part storing the ionic liquid, and a step of adhering the fraction of the ionic liquid to the solid sample, the ionic liquid portioning step and the adhering step being carried out using an ionic liquid portioning part for portioning the fraction of the ionic liquid from the pallet part and adhering the fraction to the solid sample.

In the sample observation method, in a case where the solid sample is formed of a porous material, the ionic liquid adhering step includes a step of impregnating the ionic liquid into the solid sample.

In the sample observation method, the thermal conductivity of the ionic liquid is higher than the thermal conductivity of the solid sample.

Moreover, the embodiment is also directed to a sample observation method which includes an ionic liquid adhering step of adhering an ionic liquid to an ionic liquid holding member having an opening, and a surface observing step of magnifying and observing the ionic liquid, the ionic liquid adhering step including a step of filling the ionic liquid into the interior of the opening, wherein the sample observation method includes a step of observing the sample in a state where the sample is floating in the ionic liquid by being dispersed in the ionic liquid or on the surface of the ionic liquid.

In the sample observation method, the ionic liquid adhering step includes an ionic liquid portioning step of portioning a fraction of the ionic liquid from a pallet part storing the ionic liquid, and a step of adhering the fraction of the ionic liquid to the ionic liquid holding member having the opening, the ionic liquid portioning step and the adhering step being carried out using an ionic liquid portioning part for portioning the fraction of the ionic liquid from the pallet part and adhering the fraction to the ionic liquid holding member having the opening.

The sample observation method includes a step of dispersing the sample into the ionic liquid.

The sample observation method includes a step of dispersing the sample into the ionic liquid of the pallet part.

In the sample observation method, the respective steps are performed inside a chamber which can maintain a pressure reduced-state.

The sample observation method includes a step of processing the sample using charged particle beams.

The details of the embodiments will be explained hereinafter with reference to the drawings.

Embodiment 1

Figure 1:
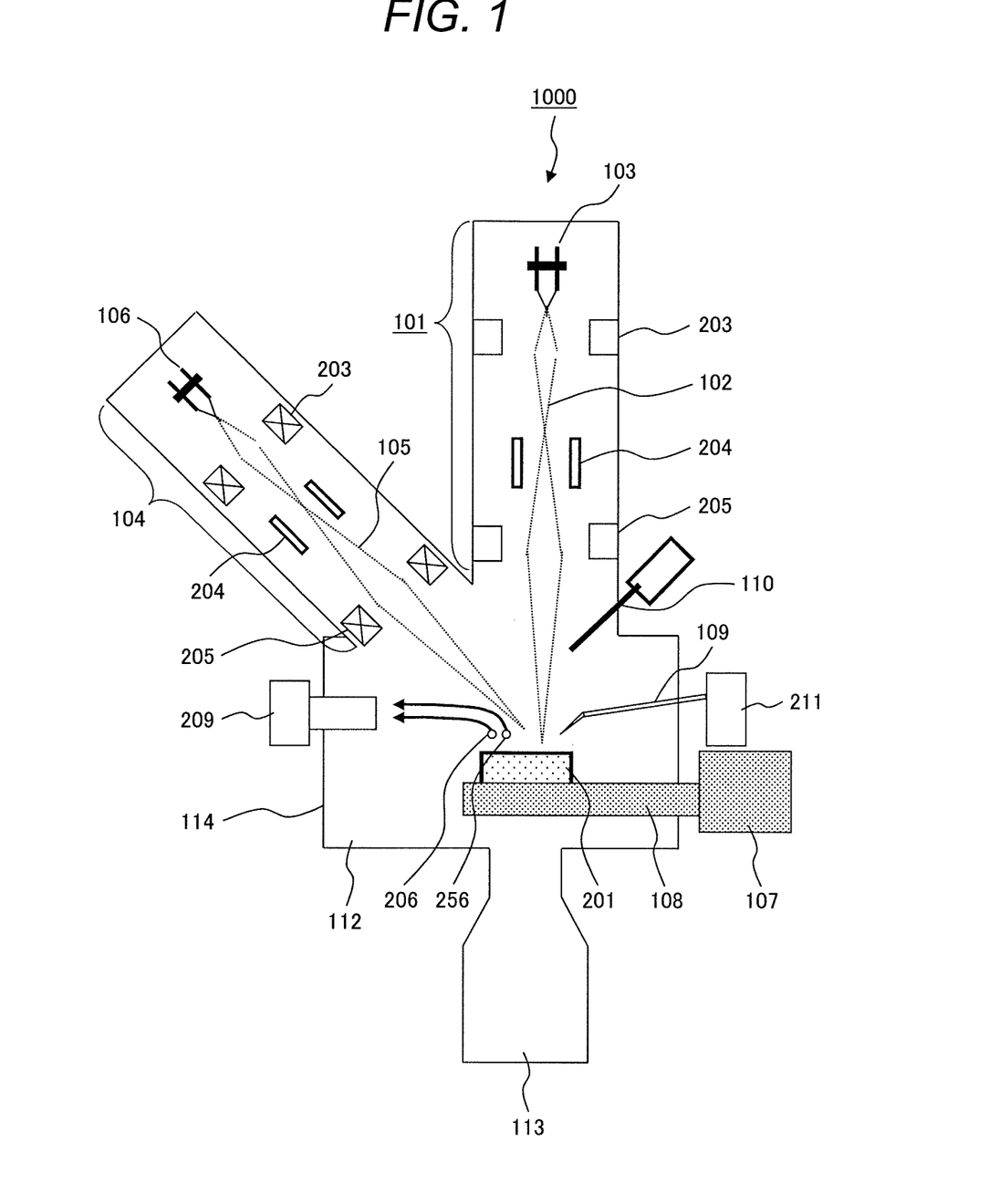
FIG. 1 is a schematic construction diagram of a charged particle beam device according to an embodiment of the present invention.

FIG. 1 is a schematic construction diagram of a charged particle beam device.

The charged particle beam device of this embodiment can be also referred to as a processing-observation device which allows operation of a mechanical probe to be performed while observing an SEM image and allows a microprocessing to be performed using an FIB device in a chamber.

Referring to this figure, the chamber 1000 includes an ion gun 101 (FIB ion gun), an electron gun 104 (SEM electron gun), and a sample chamber 112.

The ion gun 101 includes an ion source 103 from which ion beams are taken, focusing lenses 203, optical deflectors 204, and objective lenses 205.

The ion gun 101 (charged particle beam generating unit for radiating charged particle beams) is an FIB optical system element (FIB device) and configures an irradiating optical system for irradiating the ion beams 102 to a sample 201 and scanning the sample.

The electron gun 104 includes an electron source 106 for generating primary electron beams 105, optical deflectors 204 for performing beam scanning, focusing lenses 203, and objective lenses 205.

The electron gun 104 is an SEM electron optical system element and configures an irradiation optical system for irradiating the primary electron beams 105 to the sample 201 and scanning the sample.

The ion beams 102 and the primary electron beams 105 which are radiated from the ion gun 101 and the electron gun 104, respectively, are adapted to be capable of scanning on the same portion of the sample 201 arranged in the chamber 1000.

In addition, a sample stage 108 (sample supporting unit), a mechanical probe 109, a deposition gun 110 and a detector 209 are housed in the chamber 1000. An exhaust pump 113 for keeping an interior of the chamber 1000 in a pressure reduced-state (vacuum) is provided at a lower portion of the sample chamber 112. A pressure reduced-region (vacuum region) of the interior of the chamber 1000 and the outside (atmospheric pressure region) are partitioned by a vacuum chamber partition wall 114.

The ion beams 102 which are emitted from the ion source 103 are finely focused by the focusing lenses 203 and the objective lenses 205 and scan on the sample 201 by means of the optical deflectors 204. The processing of the sample is performed using a sputtering phenomenon which is produced by striking of the radiated ion beams 102 against the sample 201. A secondary charged particle beam 206 which is emitted from the sample 201 subjected to the scanning is grasped by the detector 209 in which an image is formed. Moreover, a secondary electron 256 which is generated from the sample 201 by the irradiation of the primary electron beams 105 is also detected by the detector 209.

Movement of the sample 201 is performed by the sample stage 210 which is adapted to be controlled by a slight movement control unit 107. The mechanical probe 109 which is movable in 3-axial (X, Y, Z) directions is arranged in the neighborhood of the sample 201 in the sample chamber 112 and driven under the control of a mechanical probe drive control unit 211.

Moreover, the mechanical probe 109 includes an ionic liquid portioning part for portioning a fraction of the ionic liquid and adhering it to the sample (solid sample) 201 or an ionic liquid holding member having an opening, an arm part for moving the ionic liquid portioning part, and a support part for supporting the arm part. That is, the mechanical probe 109 can be used as an ionic liquid supplying unit.

Moreover, the deposition gun 110 can be used as a sample supplying unit for dispersing a particle-shaped sample into a thin film of ionic liquid formed in the opening.

Incidentally, as will be discussed hereinafter, an attachment which is fixed to the mechanical probe 109 sprays a tungsten compound gas or a carbon compound gas from the deposition gun 110 and reacts it with the ion beams 102, namely, the attachment performs so-called ion beam assist deposition.

Moreover, the embodiment is not limited to the case where the SEM, FIB and a composite device thereof are used, and the embodiment has only to include the mechanical probe 109 having a high operation precision, and a mechanism capable of observing the operation. Therefore, the observation device (observation unit) is not always a system that performs the observation at high magnification, such as the SEM, and may be an optical microscope that can chronologically observe the operation of the mechanical probe. In this case, the sample chamber 112 is not required to be vacuum-exhausted, so that this system is suitable particularly for use in a case where the sample is required to be processed at atmospheric pressure.

Figure 2:
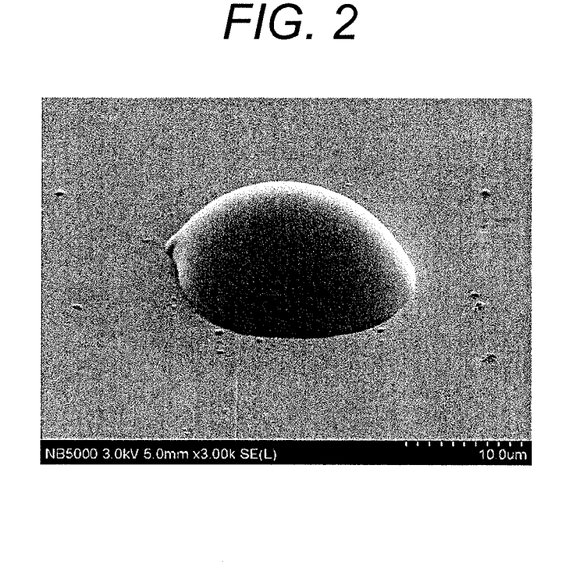
FIG. 2 is an SEM image of an ionic liquid dropped on a grid which is installed in the charged particle beam device of the embodiment.
Figure 3:
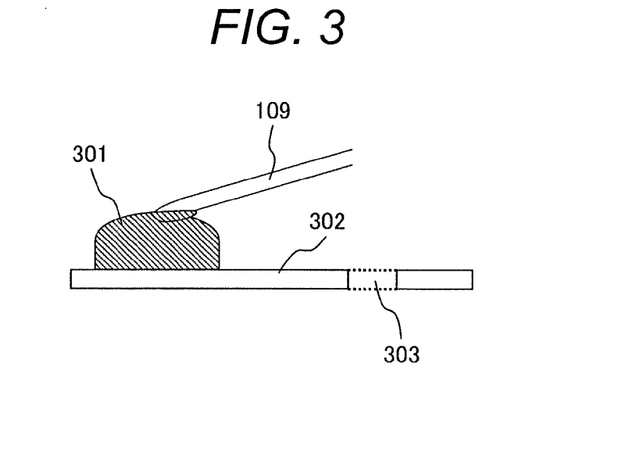
FIG. 3 is a side view which illustrates a step of portioning the ionic liquid using a mechanical probe of the embodiment.
Figure 4:
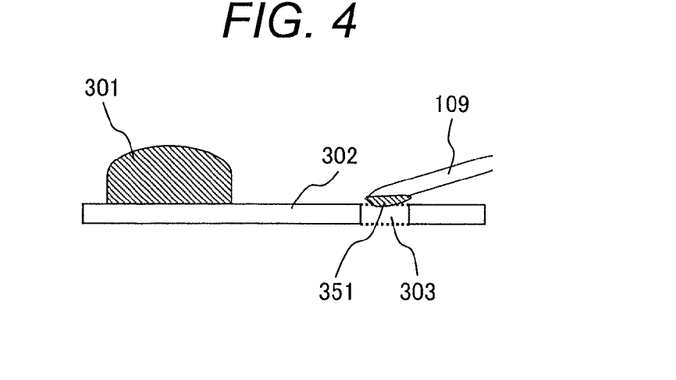
FIG. 4 is a side view which illustrates a step of adhering the ionic liquid to an opening of an ionic liquid holding member, using the mechanical probe of the embodiment.

FIG. 2 is an SEM image of an ionic liquid dropped (applied) on a grid (microgrid or mesh) in a stage prior to a step of portioning the ionic liquid using the mechanical probe. FIG. 3 is a side view which illustrates the step of portioning the ionic liquid using the mechanical probe. FIG. 4 is a side view which shows the step of adhering the ionic liquid to the opening of the ionic liquid holding member using the mechanical probe.

In this embodiment, the step of adhering the ionic liquid to the ionic liquid holding member having the opening is referred to as an ionic liquid adhering step.

First of all, the ionic liquid is dropped (applied) on apart of the grid (referred to as a pallet part). The dropped ionic liquid becomes a state where it is thickly swelled on the order of few micrometers as seen from the SEM image of FIG. 2. The pallet part is a part which stores the ionic liquid in the chamber, and a part of the grid (ionic liquid holding member) may be employed as the pallet part.

Approaching of the mechanical probe 109 to the ionic liquid 301 in the swelled-state is performed while viewing the SEM image and the ionic liquid 301 is adhered to the tip end of the mechanical probe 109 (FIG. 3). The mechanical probe 109 with the tip end having the ionic liquid 351 adhered thereto is brought to approach the opening 303 of the grid 302 (ionic liquid holding member) and fills (applies) the ionic liquid 351 into the opening 303 (FIG. 4). Namely, in this embodiment, the ionic liquid adhering step includes a step of forming a thin film of the ionic liquid 301 in an interior of the opening 303.

Figure 5:
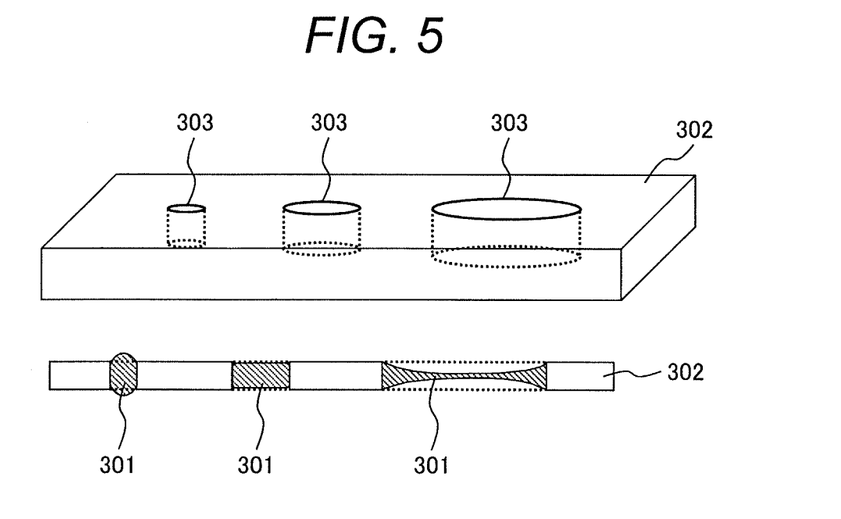
FIG. 5 is a perspective and sectional view showing a state where films of ionic liquid which have different thicknesses are formed by varying the diameters of openings of the ionic liquid holding member.
Figure 6:
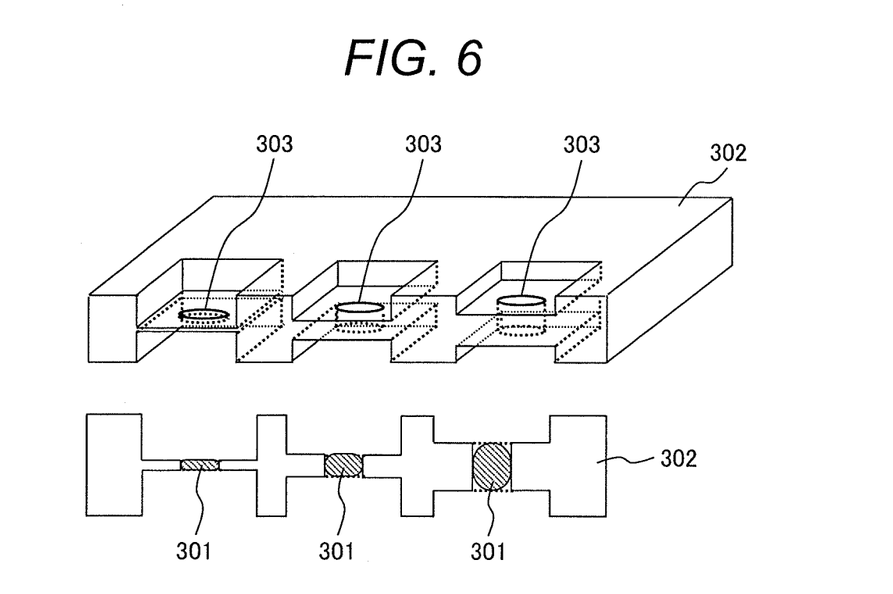
FIG. 6 is a perspective and sectional view showing a state where films of ionic liquid which have different thicknesses are formed by varying the thicknesses of the openings of the ionic liquid holding member.

FIGS. 5 and 6 illustrate a process for adjusting the shapes of openings of the grid and controlling the thickness of the ionic liquid droplets.

FIG. 5 is a perspective and sectional view showing a state where films of the ionic liquid which have different thickness are formed by varying the diameters of the openings of the ionic liquid holding member. FIG. 6 is a perspective and sectional view showing a state where films of the ionic liquid which have different thicknesses are formed by varying the thicknesses of the openings of the ionic liquid holding member.

Usually, the sample is fixed to the grid 302 and can be observed in the device.

Holes 303 (openings) in the order of few micrometers as shown in FIG. 5 are previously formed in regions of the grid 302 by using the FIB device. The diameters and shapes of the holes 303 are optional. The diameters of the holes 303 are varied, thus making it possible to adjust the thicknesses of portions of films of the ionic liquid 301 which are adjacent to centers of the films.

Moreover, if the regions of the grid 302 are previously made thin prior to the forming of the holes 303, as shown in FIG. 6, the films of the ionic liquid 301 which are to be formed can be made thinner. Moreover, by adjusting the thickness of the grid 302, it is also possible to adjust the thicknesses of the films of the ionic liquid 301 which are to be formed.

Thus, the ionic liquid droplets 301 which are filled into the holes 303 can be formed as ionic liquid thin-films which have thicknesses of 100 nm or less at center parts thereof, due to the action of surface tension.

In this embodiment, the ionic liquid adhering step includes an ionic liquid portioning step of portioning a fraction of the ionic liquid from a pallet storing the ionic liquid, and a step of adhering the fraction of the ionic liquid to the ionic liquid holding member having the openings, the ionic liquid portioning step and the adhering step being carried out using an ionic liquid portioning part for portioning the fraction of the ionic liquid from the pallet part and adhering the ionic liquid to the ionic liquid holding member having the openings. A particle-shaped sample may be previously dispersed in the ionic liquid of the pallet part Embodiment 2

This embodiment is directed to a process in which processing of an atmospherically easy-denatured sample is performed using the FIB device and, thereafter, applying of the ionic liquid to the sample is performed in the vacuum chamber, to thereby protect the surface of the sample.

The fundamental process of this embodiment is the same as that of the embodiment 1 and points different from the embodiment 1 will be mainly explained hereinafter.

Figure 7:
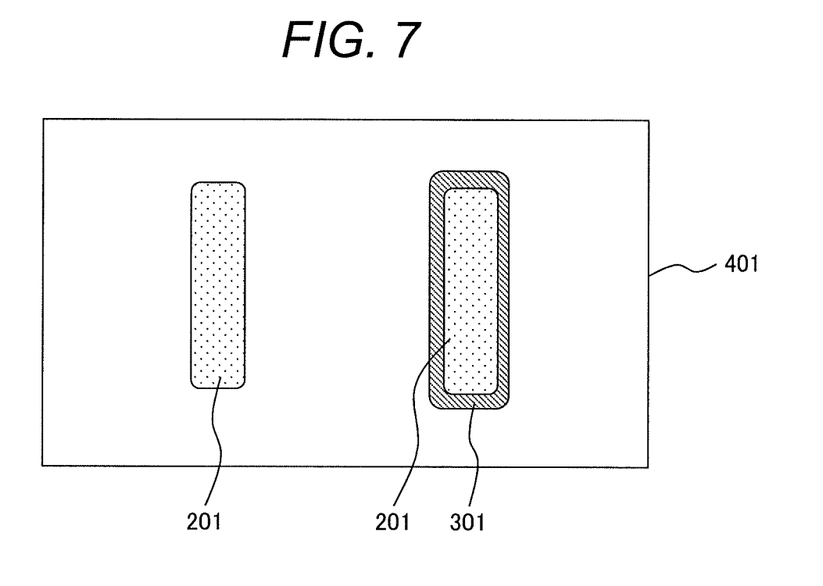
FIG. 7 is a top plane view showing a solid sample to which the ionic liquid is applied.

FIG. 7 is a top plane view showing a solid sample (merely referred to as a sample) to which the ionic liquid is applied.

Figure 8:
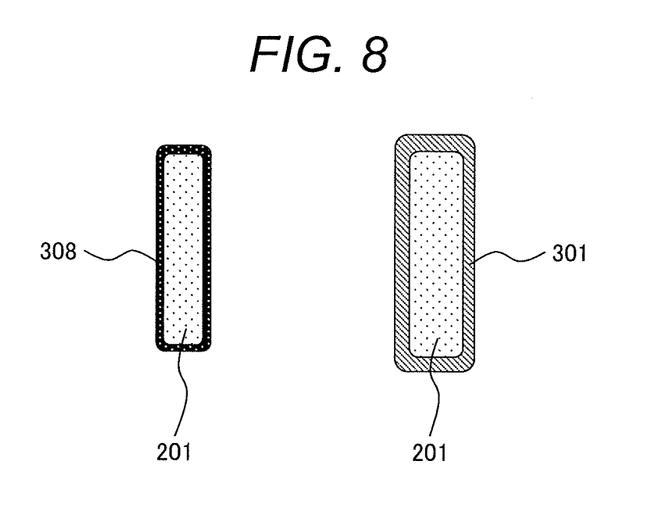
FIG. 8 is a top plane view showing a state where the solid sample to which the ionic liquid is applied is exposed to an atmosphere.

FIG. 8 is a top plane view showing a state where a solid sample to which the ionic liquid is applied is exposed to an atmosphere.

FIG. 7 shows the states of atmospherically easy-denatured samples (samples are easily subject to morphological change (contamination, oxidation, etc.)) under vacuum conditions immediately after the processing of the samples is performed using the FIB device. In this figure, a sample 201 on the left side in a sample stage 401 is not treated (without coating) and a sample 201 on the right side is coated with an ionic liquid 301.

As shown in FIG. 7, even if the samples 201 are subject to the morphological change (contamination, oxidation, etc.) by contact with the atmospheric air, the cross sections and thin-film formation surfaces of the samples immediately after being prepared by the FIB are clean and the state is maintained for a predetermined period of time in the chamber which has only to be vacuum-exhausted.

Moreover, FIG. 8 shows the state where the samples 201 are exposed to the atmospheric air. In this figure, the sample 201 on the left side is not treated (without coating) and the sample 201 on the right side is coated with an ionic liquid 301.

In the case where the non-treated sample 201 (without coating) is exposed to the atmosphere as shown in FIG. 8, the morphological change (contamination, oxidation, etc.) is immediately produced on a sample surface part 308. On the other hand, even if the sample which has been coated with the ionic liquid 301 is exposed to the atmosphere, a film of the ionic liquid 301 makes isolation between the sample surface part 308 and the atmosphere, so that the morphological change (contamination, oxidation, etc.) is difficult to be produced.

Next, the ionic liquid adhering step is explained.

In this embodiment, it is preferable that the ionic liquid is applied to the sample surface in such a manner that the film of the ionic liquid is not made too thick, by the probe operation in the same manner as the probe operation performed in the embodiment 1.

Moreover, by optionally changing the shape of the tip end part (also referred to as an ionic liquid portioning part) of the mechanical probe, or attaching any attachment having separate function to the tip end part, it is possible to adjust an ionic liquid applied-area or an ionic liquid applying amount.

Figure 9:
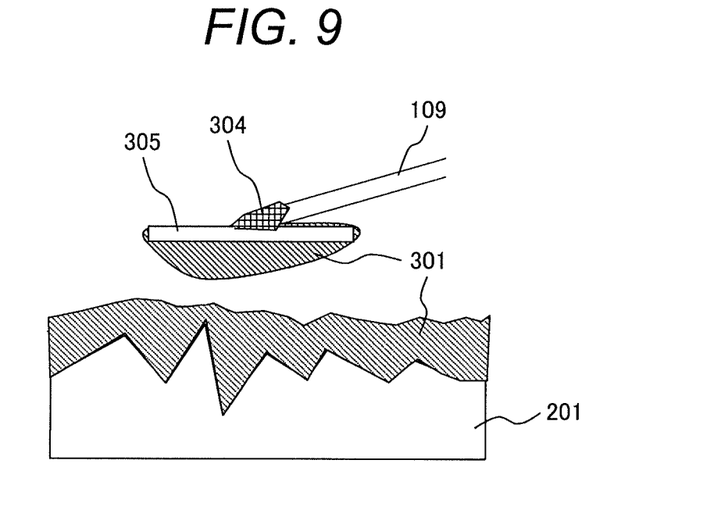
FIG. 9 is a side view which shows a step of applying the ionic liquid to a solid sample using a mechanical probe whose tip end part is formed in a flat plate-shape.

For example, as shown in FIG. 9, when a plate-shaped (flat plate-shaped) attachment 305 which has a large area is attached to the tip end part of the probe 109, a retaining amount of the ionic liquid 301 can be increased and application (coating) of the ionic liquid to a wide region of the sample 201 can be made.

Figure 10:
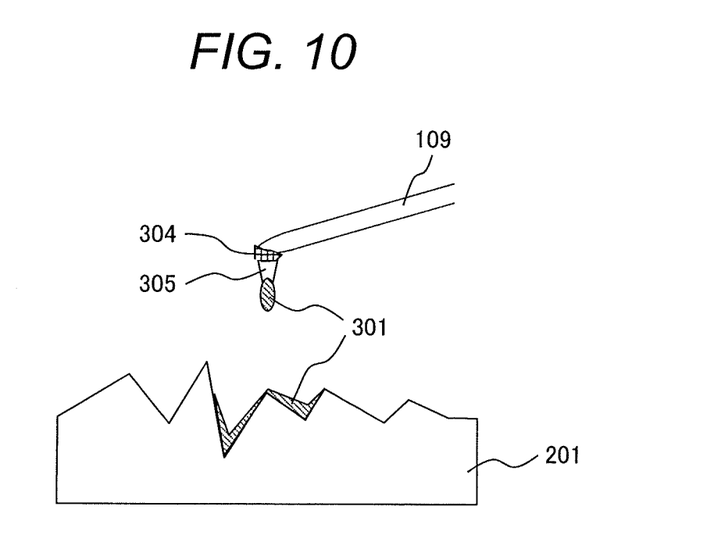
FIG. 10 is a side view which shows a step of adhering the ionic liquid to a solid sample using a mechanical probe whose tip end part is formed in a needle-shape.

Moreover, when such a sharp point shaped (needle-shaped) attachment 305 as to be shown in FIG. 10 is attached to the tip end part of the probe 109, it is possible to apply a very thin film of the ionic liquid 301 to the sample 201 in a pin-point manner. Adhesion between the probe 109 and the attachment 305 can be performed by an FIB deposition 304 or the like.

As described above, the shape of the ionic liquid portioning part may be a flat-shape or a needle-shape and, though not shown, maybe a plate shape having a curved surface (a curved shape). By selecting a suitable shape as that of the ionic liquid portioning part, it is possible to form a thin film of the ionic liquid (having a film thickness of 100 nm or less) on the surface of the solid sample.

Figure 11:
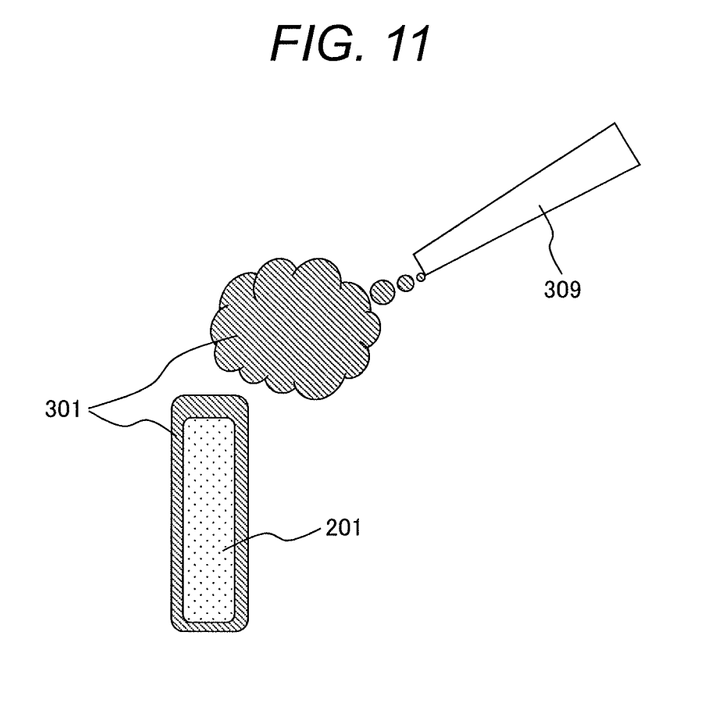
FIG. 11 is a schematic diagram which illustrates a step of adhering the ionic liquid to a solid sample using an ink jet nozzle.

Incidentally, unless the application of the ionic liquid 301 is limited to a case where the ionic liquid is applied to a specified microscopic region, in addition to the process which employs such a probe 109 as to be described above, a very thin film of the ionic liquid 301 maybe formed on an entire surface of a sample 201, using an ionic liquid-vapor jetting port (ink jet nozzle) 309 (a sprayer may be used) as shown in FIG. 11. That is, the ink jet nozzle may be used as the ionic liquid supplying unit.

When the conventional process is employed, an amount of the ionic liquid to be applied on a sample surface is made too much, so that there are arisen adverse effects of limiting an observation view and a sample structure, and difficulty in observing at high magnification. However, according to this embodiment, it is possible to form a very thin ionic liquid-film on an arbitrary sample-surface and high magnification observation is possible at an arbitrary position.

After the above-mentioned ionic liquid adhering step, the surface of the solid sample is magnified and observed in the surface observation step.

Incidentally, the ionic liquid adhering step shall include a step of forming an ionic liquid in the form of a thin-film on at least a part of the surface of the solid sample.

Moreover, the ionic liquid adhering step may include an ionic liquid portioning step of portioning a fraction of the ionic liquid from a pallet part storing the ionic liquid, and a step of adhering the fraction of the ionic liquid to the solid sample, the ionic liquid portioning step and the adhering step being carried out using an ionic liquid portioning part for portioning the fraction of the ionic liquid from the pallet part and adhering the fraction to the solid sample.

Embodiment 3

This embodiment is directed to a process in which the ionic liquid is applied to irregularities of the surface of the sample to thereby flatten the surface of the sample.

The fundamental process of this embodiment is the same as those of the embodiments 1 and 2, and points different from the embodiments 1 and 2 will be mainly explained hereinafter.

Figure 12:
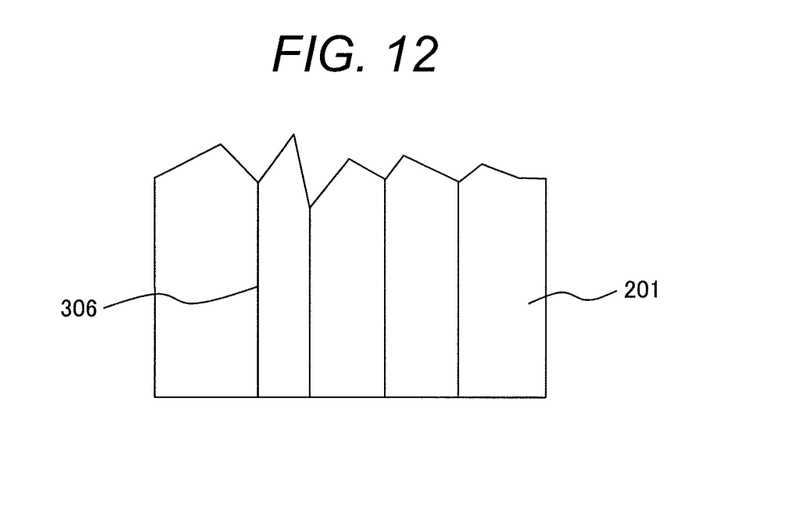
FIG. 12 is a schematic sectional view which shows a neighborhood of a surface of a solid sample to which an ion beam is irradiated.
Figure 13:
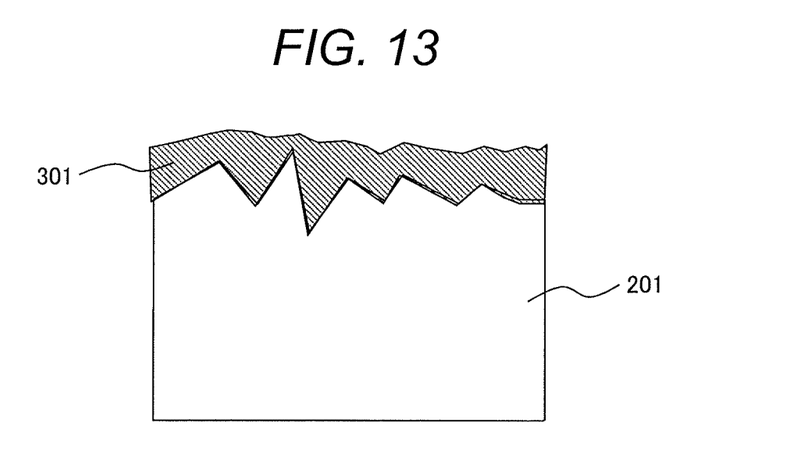
FIG. 13 is a schematic sectional view which shows a neighborhood of a surface of a solid sample to which an ion beam is irradiated after the ionic liquid is applied to the solid sample.

When a sample 201 having irregularities on a surface thereof is processed by charged particle beams, processing damages (processing lines) 306 are easy to be produced from the irregularities (FIG. 12). Therefore, in this embodiment, a film of the ionic liquid 301 is formed on the surface of the sample 201 (FIG. 13).

In this case, if the film is too thick, processing of the sample 201 itself takes a lot of time. In addition, the irregularities are easy to be produced on a processed cross section and confirmation of the structure of the sample 201 becomes difficult.

Therefore, the film forming is performed while controlling the thickness of the film in such a manner that the film has a minimum thickness. It is desirable that the film thickness is in the order of few hundred nanometers to 1 μm.

According to this embodiment, in the formation of a sample cross section and a thin film sample which is performed using the charged particle beam device including the FIB device, it is possible to flatten the irregularities and possible to prevent the damages of the surface of the sample which are caused by irradiation of charged particle beams.

Embodiment 4

This embodiment is directed to a process in which, in a case where a sample is a porous material, the ionic liquid is impregnated into pores of the sample.

The fundamental process of this embodiment is the same as those of the embodiments 1-3 and points different from the embodiments 1-3 will be mainly explained hereinafter.

Figure 14:
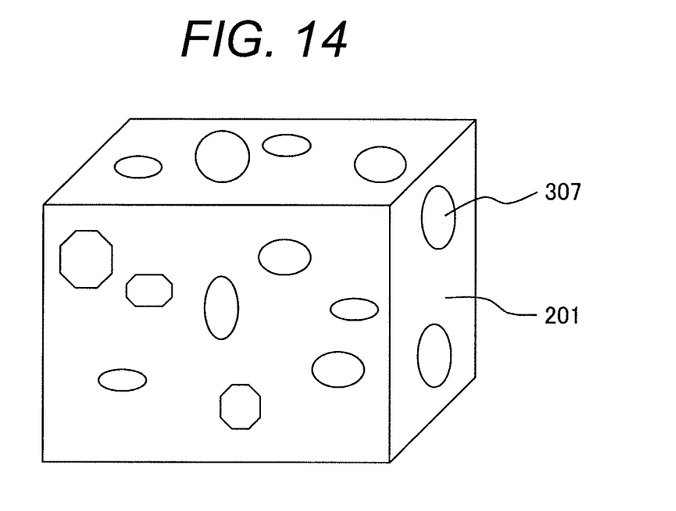
FIG. 14 is a schematic perspective view which illustrates a solid sample formed of a porous material.

FIG. 14 shows a case where the sample 201 is a porous material having pores 307.

Figure 15:
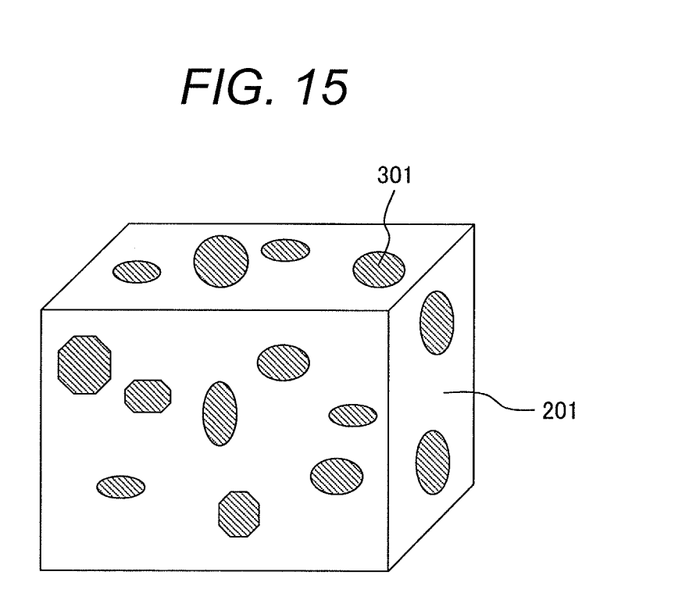
FIG. 15 is a schematic perspective view showing a state where the ionic liquid is impregnated in the solid sample which is formed of the porous material.

FIG. 15 illustrates a state where liquid material (ionic liquid 301) is impregnated into the pores 307 from the surface of the sample 201, to thereby fill up the pores 307 with the liquid material. In this case, the ionic liquid 301 is a thermal conductive medium.

Thus, the thermal conductivity of the sample 201 is increased, heat accumulated at a part of the sample which is subjected to the irradiation of the charged particle beams rapidly spreads to a circumferential part, to thereby suppress partial temperature rising, and reduction in deformation of the structure of the sample is made possible.

According to this embodiment, it is possible to prevent the deformation and denaturation in the sample 201 (porous material) which is formed of polymer or the like that is subject to the deformation of the structure and material denaturation by heat.

In this embodiment, control of the thickness of the ionic liquid film is performed by using the process of applying the ionic liquid to the sample as in the embodiment 2. The ionic liquid has a low viscosity, so that by applying the ionic liquid to the sample made of the porous material from the sample surface, to thereby cause the ionic liquid to be impregnated into the interior of the sample, it is possible to fill up the voids (pores) with the ionic liquid.

In this case, it is possible to make an application amount of the ionic liquid minimum using the mechanical probe. The application process is not limited to the process performed using the mechanical probe and the thin film of the ionic liquid may be formed on the surface of the sample by employing the principle of the spray process and the ink jet process which has been described with respect to the embodiment 2 and FIG. 11.

According to this embodiment, in the deposition process including the FIB and CVD, it is possible to thinly control the film thickness and impregnate the ionic liquid into the interior of the porous material.

According to this embodiment, in the observation by the SEM, it is possible to considerably reduce the amount of the application of the ionic liquid to the sample surface, possible to observe an original surface structure of the sample in the state where the ionic liquid is applied to the sample, and possible to perform the high-resolution observation.

According to the above-mentioned embodiments (embodiments 1-4), it is possible to control the volume of the ionic liquid to be applied to the sample.

Moreover, according to the above-mentioned embodiments, it is possible to bring the ionic liquid to a superthin film-state (film thickness: 100 nm or less) and, moreover, possible to cause the sample to be carried on the ionic liquid in the superthin film-state and observe the behavior of the sample in the liquid at the atomic level.

Moreover, according to the above-mentioned embodiments, it is possible to protect the surface of the sample with the ionic liquid in the superthin film-state to prevent the contact between the sample and the atmosphere, and possible to cause a liquid retaining-state of the sample to be maintained.

Moreover, according to the above-mentioned embodiments, it is possible to reduce the damages of the sample which are caused by the irradiation of the charged particle beams, particularly, FIB (Focused Ion Beam), and a charge-up (including a charge-up in the observation by an electron microscope).

Moreover, according to the above-mentioned embodiments, it is possible to reduce the deformation of the solid sample by impregnating the ionic liquid into the solid sample formed of the porous material and filling up the pores or voids in the solid sample with the ionic liquid.

Moreover, according to the above-mentioned embodiments, when the sample is observed by the charged particle beam device, the observation is not performed by spreading the observation target sample to an organic polymeric membrane such as a collodion membrane which is a solid, and the observation uses the ionic liquid which is liquid, as a support film, so that the support film is not deformed and the original shape of the sample can be observed.

Moreover, according to the above-mentioned embodiments, it is possible to make the thickness of the film of the ionic liquid to be applied to the sample very thin and the high-resolution observation by the SEM, TEM, STEM, etc. is possible.

Reference Signs List

101: Ion gun, 102: Ion beam, 103: Ion source, 104: Electron gun, 105: Primary electron beam, 106: Electron source, 107: Slight movement-control unit, 108: Sample stage, 109: Mechanical probe, 110: Deposition gun, 112: Sample chamber, 113: Vacuum exhaust pump, 114: Vacuum chamber partition wall, 201: Sample, 203: Focusing lens, 204: Optical deflector, 205: Objective lens, 206: Secondary electron, 209: Detector, 210: Sample stage, 211: Mechanical probe drive control unit, 301: Ionic liquid, 302: Ionic liquid holding member, 303: Opening, 304: FIB deposition, 305: Attachment, 306: Processing damage, 307: Pore, 308: Sample surface part, 309: Ionic liquid vapor jetting port, 1000: Chamber

The invention claimed is:

1. A charged particle beam device comprising:
   an ionic liquid holding member having an opening;
   an ionic liquid supplying unit for filling an ionic liquid into the opening;
   an observation unit for observing an adhesion state of the ionic liquid; and
   a charged particle beam generating unit for radiating charged particle beams,
   wherein a thickness of a droplet of the ionic liquid to be filled in the opening can be adjusted for observing a sample in a state where the sample is floating in the ionic liquid by being dispersed in the ionic liquid or on a surface of the ionic liquid,
   wherein the ionic liquid supplying unit is a mechanical probe which includes an ionic liquid portioning part for portioning a fraction of the ionic liquid from a pallet part storing the ionic liquid and for filling the fraction into the opening; an arm part for moving the ionic liquid portioning part; and a support part for supporting the arm part, and
   wherein the ionic liquid portioning part is adapted to be capable of mainly filling the ionic liquid into the opening.

2. The charged particle beam device according to claim 1, wherein a shape of the ionic liquid portioning part is a flat plate-shape, a curved surface-shape, or a needle-shape.

3. The charged particle beam device according to claim 1, including a sample supplying unit for dispersing the sample into the ionic liquid or on the surface of the ionic liquid.

4. The charged particle beam device according to claim 1, wherein an inner diameter of the opening is 1 to 10 μm.

5. The charged particle beam device according to claim 1, wherein the ionic liquid has a thermal conductivity higher than that of the sample.

6. The charged particle beam device according to claim 1, wherein the ionic liquid holding member, the ionic liquid supplying unit, the observation unit, and the charged particle beam generating units are installed in a chamber which can keep them in a pressure reduced-state.

7. A sample observation method comprising:
   an ionic liquid adhering step of adhering an ionic liquid to a solid sample; and
   a surface observing step of magnifying and observing a surface of the solid sample,
   wherein the ionic liquid adhering step includes a step of forming the ionic liquid in form of a thin film on at least a part of the surface of the solid sample, wherein the ionic liquid adhering step includes an ionic liquid portioning step of portioning a fraction of the ionic liquid from a pallet part storing the ionic liquid; and a step of adhering the fraction of the ionic liquid to the solid sample, the ionic liquid portioning step and the adhering step being carried out using an ionic liquid portioning part for portioning the fraction of the ionic liquid from the pallet part and adhering the fraction to the solid sample.

8. The sample observation method according to claim 7, wherein the solid sample is formed of a porous material, and
wherein the ionic liquid adhering step includes a step of impregnating the ionic liquid into the solid sample.

9. The sample observation method according to claim 7, wherein the ionic liquid has a thermal conductivity higher than that of the solid sample.

10. A sample observation method comprising:
an ionic liquid adhering step of adhering an ionic liquid to an ionic liquid holding member having an opening; and
a surface observing step of magnifying and observing the ionic liquid,
the ionic liquid adhering step including a step of filling the ionic liquid into the opening,
wherein a sample is dispersed into the ionic liquid or on a surface of the ionic liquid and observed in a state that the sample is floating in the ionic liquid,
wherein the ionic liquid adhering step includes an ionic liquid portioning step of portioning a fraction of the ionic liquid from a pallet part storing the ionic liquid; and a step of adhering the fraction of the ionic liquid to the ionic liquid holding member having the opening, the ionic liquid portioning step and the adhering step being carried out using an ionic liquid portioning part for portioning the fraction of the ionic liquid from the pallet part and adhering the fraction to the ionic liquid holding member having the opening.

11. The sample observation method according to claim 10, including a step of dispersing the sample into the ionic liquid.

12. The sample observation method according to claim 10, including a step of dispersing the sample into the ionic liquid of the pallet part.

13. The sample observation method according to claim 7, wherein the respective steps are performed in a chamber which can keep a pressure reduced-state.

14. The sample observation method according to claim 7, wherein processing of the sample is performed using a charged particle beam.

15. A charged particle beam device comprising:
an ionic liquid holding member having an opening;
a pallet part storing the ionic liquid;
a mechanical probe which includes an ionic liquid portioning part for portioning a fraction of the ionic liquid from the pallet part;
an observation unit for observing an adhesion state of the ionic liquid; and
a charged particle beam generating unit for radiating charged particle beams,
wherein the ionic liquid portioning part is adapted to be capable of filling the fraction into the opening.

16. The charged particle beam device according to claim 15,
wherein the ionic liquid holding member has plural opening which have different diameters respectively.

17. The charged particle beam device according to claim 15,
wherein the ionic liquid holding member has plural openings which have different thicknesses respectively.

18. The charged particle beam device according to claim 15,
wherein the opening is arranged at a thinner part of the ionic liquid holding member.

19. The charged particle beam device according to claim 15,
wherein a shape of the ionic liquid portioning part is a flat plate-shape, a curved surface-shape, or a needle-shape.

20. The charged particle beam device according to claim 15,
wherein attachments which have different shapes respectively can be attached to the ionic liquid portioning part.

* * * * *